United States Patent [19]

Curtiss et al.

[11] Patent Number: 4,861,596

[45] Date of Patent: Aug. 29, 1989

[54] ROLLED MATRIX DEVICE HAVING ENHANCED ABILITY TO UNROLL AND METHOD FOR ITS PRODUCTION

[75] Inventors: Alan C. Curtiss; Jeelin Lo, both of Old Lyme, Conn.

[73] Assignee: Pfizer Inc., New York, N.Y.

[21] Appl. No.: 170,529

[22] Filed: Mar. 21, 1988

[51] Int. Cl.⁴ ............................................... A61K 9/24
[52] U.S. Cl. ................................... 424/438; 427/387; 428/448; 428/516; 424/422
[58] Field of Search ...................... 424/438; 427/387; 428/137, 447, 516, 448

[56] References Cited

U.S. PATENT DOCUMENTS 4,228,149 10/1980 Brewer et al. ...................... 424/438
4,601,893 7/1986 Cardinal .............................. 424/438

Primary Examiner—Marion C. McCamish
Assistant Examiner—Dean Cornstubble
Attorney, Agent, or Firm—Peter C. Richardson; J. Trevor Lumb; Albert E. Frost

[57] ABSTRACT

A method for enhancing the unrolling of a rolled active agent-containing laminate device in an aqueous use environment which comprises coating one side of the device with an elastomer prior to constraining it in a rolled configuration; and the devices so treated.

14 Claims, No Drawings

ROLLED MATRIX DEVICE HAVING ENHANCED ABILITY TO UNROLL AND METHOD FOR ITS PRODUCTION

BACKGROUND OF THE INVENTION

1. Field of the Invention

This invention relates to a method for enhancing the unrolling of a controlled release active agent-containing polymer matrix device in an aqueous environment, the device being constrained in a rolled configuration prior to placement in said environment. More particularly, it relates to a method for enhancing the unrolling of such an active agent-containing polymer matrix device, including a laminate device, in an aqueous environment, the device being constrained in a rolled configuration prior to placement in said environment which comprises coating one side of the device with an elastomer prior to constraining it in a rolled configuration.

2. Description of the Prior Art

Administration of an active agent to a use environment in such a manner that the agent is released in a controlled manner over a prolonged period of time is well known in the veterinary pharmaceutical and medical arts. A large variety of devices have been developed for achieving the desired result. Representative of such devices of value for use in a mammalian system, and especially in ruminant animals, are variable geometry devices of the polymer matrix type. Particularly valuable for use in ruminant animals are matrix type devices having a size and composition which permit them to be constrained to a size and shape suitable for oral administration to a mammal and which, when in the use environment, revert to their original or near-original pre-constrained shape. Included in the term matrix devices as used herein are laminated matrix devices.

Variable geometry matrix devices of the type referred to above are disclosed in U.S. Pat. No. 4,228,149, issued Oct. 14, 1980. Laminate devices comprising an active agent containing resilient polymeric sheet and a polymer film coating one or both sides of said sheet are also disclosed in said patent. Perforated laminate devices are described in U.S. Pat. No. 4,601,893, issued July 22, 1986. The disclosures of each of said patents is incorporated herein by reference.

Preferred matrix devices of the non-laminate type of U.S. Pat. No. 4,228,149, referred to herein as "simple" matrix devices, are those wherein the device comprises a resilient sheet of ethylene vinylacetate (EVA) copolymer as the medium in which the active agent is dispersed. Preferred laminate type devices described in said patent are those wherein the active agent-containing sheet is coated on one or both surfaces with EVA, but not on the edges.

Preferred laminate devices of U.S. Pat. No. 4,601,893 are those wherein the active agent-containing core sheet is EVA. Particularly preferred are those devices wherein the core sheet is coated on both surfaces by films of EVA.

The devices described in the above-cited patents, all oral delivery devices for controlled release of an active agent to a ruminant animal are, as initially manufactured, generally rectangular in shape. To permit their oral administration they are rolled to a cylindrical or substantially cylindrical shape; i.e., a rolled configuration, and constrained in such shape by constraining means. For this reason, the flexibility, and especially the resiliency, of the polymer sheet which comprises the matrix or the core sheet of a laminate device are important as regards the ability of the constrained device to unroll in the use environment, e.g., the rumeno-reticular sac, once the constraining means operates to release the constrained laminate.

Suitable constraining means are, for example, biodegradable string, tape or glue, water soluble adhesive, paper or gelatin capsules.

The herein-described devices can be used to administer a variety of drugs to ruminants. Representative of the active agents which can be used in the devices described herein are anthelmintics, antibacterials, beta-lactams, aminoglycosides, antibacterial growth promotants, antiparasitic agents, essential minerals, vitamins, sulfa drugs, larvacides and insecticides.

The devices described herein offer a practical and especially valuable means for the control (therapeutic and prophylactic) of helminth infections in ruminant animals, cattle in particular. For this purpose anthelmintics, including salts thereof, such as morantel, pyrantel, levamisole, tetramisole, oxantel, ivermectin, piperazine and diethyl carbamazine are of great value.

The constrained devices when placed within the use environment should unroll to their original or near-original rectangular shape so as to permit retention of the device in the rumeno-reticular sac for a prolonged period. However, upon prolonged storage in a constrained shape they tend to set; i.e., to lose their resiliency, and the ability to unroll to a cross-section diameter within a relatively brief period, about two hours, following their administration sufficient to ensure their retention in the rumenoreticular sac and to prevent regurgitation of the device. Thus, the matrix devices of the art undergo an aging process, which process is a function of time and temperature, which reduces their ability to unroll in the use environment, e.g., the rumen, to a size adequate for retention.

SUMMARY OF THE INVENTION

It has now been found that the ability of the herein-described constrained matrix, including laminate, devices to unroll in a use environment even after prolonged periods of storage is markedly enhanced if the devices are coated on one side with an elastomer prior to their being constrained in a rolled configuration. The elastomer coated side improves the elasticity of the devices such that they recover or unroll from their constrained configuration to a greater extent and at a faster rate. The term "elastomer" as used herein is intended to embrace materials that, when stretched, snap back to their original or near-original shape. More specifically, it embraces thermoset and thermoplastic elastomers or elastoplastics, representative of which are silicones, e.g polydimethylsiloxanes, styrene-diene block copolymers, polyurethanes, nitrile rubbers, olefinics and copolyester ethers.

Included within the scope of this application are matrix, including laminate, devices of the type described above which have been subjected to tensile stress prior to being constrained in a rolled configuration. Such stressed devices are reported to require a lesser charge of active agent to achieve a given release rate than do non-stressed devices of like construction. They are disclosed in pending U.S. patent application Ser. No. 925,776, filed Oct. 30, 1986.

DETAILED DESCRIPTION OF THE INVENTION

The process of this invention comprises coating one side of the devices with an elastomer prior to constraining them in a rolled configuration.

The herein-described process is especially useful as regards the laminate devices of U.S. Pat. No. 4,601,893 which comprise morantel or a water soluble acid addition salt of morantel such as the citrate or tartrate. In said devices, the amount of morantel in the core sheet, calculated as acid addition salt can range from 10% to 75% by weight of core sheet. It is of particular value as regards said devices wherein the core sheet and the outer laminae comprise ethylene vinylacetate (EVA) copolymer as the construction material.

The simple matrix devices are prepared by known methods, such as those described in U.S. Pat. No. 4,228,149. The procedure comprises blending the active agent, e.g. morantel citrate or tartrate, with softened preformed polymer For example, a strip of polymer is run through a roll mill which is heated to a temperature sufficient to soften the polymer without decomposing the active agent. The active agent is gradually added to the nip of the mill and the softened strip of polymer recirculated until the desired composition and homogeneity are realized. The strip is then formed into sheets of the desired dimensions.

The herein-described devices, including the laminate devices, are thin rectangular devices having two flat sides and four narrow edges. The term "side" as used herein refers to one of the flat sides and not to an edge. The elastomer coated side becomes the outer side of the device when the device is placed in a rolled configuration.

The devices are coated by bonding the chosen elastomer to a flat side of the device by means of pressure and heat or by use of a binder. The particular technique used depends upon the polymers used in the matrix device and the nature of the active agent. A binder, if used, must be inert and compatible with the polymers used in the device, the active agent and the use environment. Suitable binders are disclosed in the Encyclopedia of Polymer Science and Technology, John Wiley & Sons, 8, 1968.

When binding of the elastomer is carried out by means of pressure and heat, the conditions are, of course, determined by the composition of the device and of the elastomer.

Preferred elastomers are silicone rubbers, especially those based upon the polydimethylsiloxane structure. They are biologically and chemically inert, non-toxic and non-irritating, retain their physical properties over a broad temperature range and are available as medical grade materials. Additionally, they can be cross-linked, if desired, to provide a wider range of elastomers.

The elastomer of device is bonded to a flat surface of the matrix device by appropriate means when the device is in a flat or substantially flat position. The coated device is then rolled and constrained in such a manner that the elastomer coated side is on the outside of the device. Rolling of the coated device places the elastomer coating under stress. The force thus created permits a coated device to unroll more rapidly and to a greater extent than a non-coated device.

A modification of the coating procedure which serves to further enhancing the rolling of a coated, constrained device comprises stretching the elastomer prior to bonding it to the device. In a further method for accomplishing such modification, the elastomer is stretched and bonded to the matrix device which is also in the stretched mode.

The elastomer coated devices can, if desired, be subjected to an annealing or heating step according to the process described in the concurrently filed patent application, PC 7337 of Lo et al, entitled "Method for Enhancing the Unrolling of a Rolled Matrix Device." The annealing step can, of course, be carried out before or after coating of the device with an elastomer.

The annealing temperature can range from about 40° C. to about 80° C. A range of about 43° C. to about 60° C. is preferred. The time of annealing varies with the temperature of annealing. Further, the time and temperature vary with the manner in which the devices being annealed are arranged for the annealing step. The devices can be punched or cut to their approximate or actual size prior to annealing or the sheets from which the individual devices are punched can be annealed prior to punching out individual devices.

The preferred polymer for the simple matrix devices is EVA as described above. When the device is a laminate, EVA is preferred for the core polymer and for the outer layers of the laminate.

The dimensions of the sheets prior to their being constrained depend, of course, upon the ruminant animals for which they are intended. For bovines the overall dimensions of thickness, length and width range from 2–4 mm, 5–15 cm and 4–10 cm, respectively. For sheep suitable dimensions are from 1–3 mm, 5–10 cm and 3–8 cm, respectively. The sheets are rolled and constrained in the form of cylinders for storage and administration to ruminants. In general, the height of the cylinder equals the width of the unrolled or open sheet. The diameters of constrained devices for use in bovines are from 2.0 to 3.0 cm in diameter. Those for use in sheep are from 0.8 to 1.5 cm in diameter.

The constrained devices for use in ruminants must unroll in the rumeno-reticular sac to a cross-section diameter sufficient to prevent regurgitation. Experience has demonstrated this degree of unrolling should occur within a period of about 2 hours post dosing.

The active agent-containing layer, e.g. the core, of laminate device, is prepared in sheets as described above. The core sheet is then sandwiched between films of polymer which comprise the outer layers of the laminate. They are bonded to the core sheet by applying sufficient pressure and heat to achieve bonding without destroying the active agent or the laminate. The laminated sheet is then cut to the desired dimensions. Before or after cutting, perforations of the desired size and arrangement can be made by known techniques. The device is then rolled and constrained.

Further, if the herein-described devices are to be subjected to tensile stress, this step, in the case of a simple matrix device, is conducted on the finished sheet prior to rolling In the case of a laminate device it can be carried out on the core sheet alone, but is preferably carried out on the laminate sheet, before or after perforations are made. In each of the above cases, the tensile stress can be applied before or after the coating step. However, in order to minimize the possibility of the elastomer coat from separating from the matrix, it is desirably applied before the coating step. The tensile stress must not exceed the yield point of the polymer matrix. The stress is normally applied in only one direction, usually along the length. It can, however, be applied along the width or the bias (diagonal), or along any of said directions in step-wise or concurrent fashion. The laminate is then cut to the desired dimensions. Before or after cutting of the laminate, perforations of the desired size and arrangement are made therein by known techniques. (Porosigens, if used, are blended into the core sheet along with the desired substance).

It will be noted that while the matrix devices are heated during the process of their preparation, the level and time of heating do not constitute an annealing step. The term "annealing" as used herein is intended to mean "to temper by heating". The prior art devices, e.g. those of U.S. Pat. No. 4,228,149 and U.S. Pat. No. 4,601,893, are subjected to heat during preparation and yet the finished devices are subject to a tendency to set up on long term storage or on simulated long term storage, e.g. heating at 40° C. for 48 hours.

The unrolling of an elastomer coated perforated laminate device, whether or not subjected to tensile stress, depends to some extent upon the number of holes in the device. A device having 70 holes tends to unroll to a greater extent in a two hour period than a device having 55 or less holes.

The elastomer coated devices of this invention can also be subjected to an annealing process before or after the coating step in order to further enhance the rate and extent of unrolling of constrained devices in the use environment.

EXAMPLE 1

A 50/50 by weight mixture of EVA (Type MU-760 having 19% vinyl acetate content, available from U.S.I. Chemicals Co., 99 Park Ave., New York, N.Y. 10016) and morantel tartrate was extruded once to obtain a uniform blend. The extrudant was then chopped and re-extruded to obtain a core sheet 734 mm wide and 1.9 mm thick (28.9×0.075 inches).

An EVA (Type MU-760) film was extruded at screw temperatures (4 zones) of 210/215.6/210/215.6° C. and die temperatures (3 zones) of 226.7/237.8/226.7° C. The core sheet was then coated first one side with the extruded EVA film (0.127 mm thick) and then on the other side by compression between rollers at 50-60° C. to produce a laminate.

A layer of Silastic (9 mils thick) 382 Medical Grade Elastomer (Dow Corning) was applied to one side of the laminate with a coating knife. The Silastic was cured at 50° C. for 24 hours.

The laminated sheet was trimmed to 622.3 mm (24.5 inches) wide and then slit into 3 strips of 206 mm (8.1 inches) wide each. Each strip was passed through a puncher and then through a cutter to obtain individual devices having 40, 55 or 70 holes of 2.7 mm (0.106 inch) diameter. The dimensions of each device were 20.8 cm (8.187 inches) long, 9.5 cm (3.75 inches) wide and 2.16 mm (0.085 inch) thick.

The devices were constrained in a rolled configuration (coated side outermost) using a water soluble adhesive tape, then heat at 40° C. for 48 hours to simulate long term storage at room temperature. The devices (70 holes) were then placed in 40° C. water and the degree of unrolling of individual devices determined by measuring the cross-section diameter of the devices at varying time intervals.

| Time (min.) | Unrolling of Devices (70 holes) in Cm. | |
|---|---|---|
| | Control* | Silastic Coated |
| 0 | 2.6 | 2.8 |
| 10 | 3.4 | 5.2 |
| 30 | 3.8 | 5.9 |
| 45 | 3.9 | 6.3 |
| 60 | 4.1 | 6.6 |
| 90 | 4.2 | 6.8 |
| 120 | 4.2 | 7.2 |

*Not coated with elastomer.

EXAMPLE 2

The procedure of Example 1 was followed, but polyether urethane (Q-Thane, available from K. J. Quinn & Co., Inc., 195 Canal Street, Malden, Mass.) rather than Silastic, is used as the elastomer coating. The polyether urethane is extruded at screw temperatures of 160-210° C. and die temperatures of 171-210° C. It is attached to one side of the laminate by compressing the two between rollers at 60° C.

Coated devices thus-produced unroll faster and to a greater extent than do uncoated devices.

EXAMPLE 3

The procedure of Example 1 is repeated, three lots being prepared. One lot was cured at 40° C. for 96 hours and the other at 80° C. for 4 hours, and the third lot at room temperature for one week.

Devices from each batch unroll at a faster rate and to a greater diameter than do control devices.

We claim:

1. A method for enhancing the unrolling of an active agent-containing laminate device in an aqueous use environment, said device comprising a morantel or water-soluble acid addition salt thereof-containing polymer matrix sandwiched between ethylene vinylacetate copolymer films, said device being constrained in a rolled configuration prior to placement in said environment, comprising coating one side of the device with an elastomer prior to constraining it in a rolled configuration.

2. A method according to claim 1 wherein the elastomer is a silicone rubber.

3. A method according to claim 2 wherein the water-soluble salt of morantel is the tartrate or the citrate.

4. A method according to claim 3 wherein the elastomer coated device is subjected to a thermal curing step prior to constraining it in a rolled configuration.

5. A method according to claim 4 wherein one or a plurality of machroholes are made through the device before or after the thermal curing step.

6. A method according to claim 5 wherein the macroperforations are symmetrically distributed over the face of the device.

7. The method according to claim 6 wherein the polymer matrix comprises a 1:1 mixture of morantel tartrate and ethylene vinyl acetate and the macroperforations through the device are from about 0.5 to 10 mm in diameter.

8. A method according to claim 3 wherein the curing step is conducted at ambient temperature for a period of from about one week.

9. A laminate device for controlled release of an active agent to an aqueous use environment, said device comprising a morantel or water-soluble acid addition salt thereof-containing polymer matrix sandwiched between ethylene vinylacetate copolymer films one side of said device being coated with an elastomer.

10. A laminate device according to claim 9 wherein the active agent is morantel tartrate and the elastomer is a silicone rubber.

11. The laminate device according to claim 10 wherein one or a plurality of macroperforations are made through the device.

12. A matrix device according to claim 10 wherein the elastomer is a poly (dimethylsiloxane).

13. A matrix device according to claim 12 wherein the elastomer coated device is subjected to a temperature of from ambient temperature to 80° C. for a period of from about 96 hours to about 4 hours.

14. The matrix device according to claim 13 wherein the device is constrained in a rolled configuration.

* * * * *